United States Patent [19]

Chikama

[11] Patent Number: 4,710,807
[45] Date of Patent: Dec. 1, 1987

[54] ILLUMINATING LIGHT SUPPLY SYSTEM IN ELECTRONIC ENDOSCOPE APPARATUS

[75] Inventor: Toshio Chikama, Tokyo, Japan

[73] Assignee: Kabushiki Kaisha Machida Seisakusho, Tokyo, Japan

[21] Appl. No.: 927,267

[22] Filed: Nov. 4, 1986

[30] Foreign Application Priority Data

| Nov. 11, 1985 | [JP] | Japan | 60-250847 |
| Nov. 11, 1985 | [JP] | Japan | 60-250848 |
| Dec. 28, 1985 | [JP] | Japan | 60-293566 |
| Jan. 9, 1986 | [JP] | Japan | 61-1444 |

[51] Int. Cl.$^4$ .............................................. H04N 7/18
[52] U.S. Cl. ........................................ 358/98; 128/4; 128/6
[58] Field of Search ........................ 358/98; 128/4, 6; 362/277, 282, 322

[56] References Cited

U.S. PATENT DOCUMENTS

| 3,166,623 | 1/1965 | Waidelich, Jr. | 358/98 |
| 3,525,332 | 8/1970 | Kosaka | 128/6 |
| 4,233,650 | 11/1980 | Hagner et al. | 362/322 |
| 4,621,284 | 11/1986 | Nishioka | 128/6 |
| 4,631,582 | 12/1986 | Nagasaki et al. | 358/98 |
| 4,653,478 | 3/1987 | Nagasaki et al. | 358/98 |

Primary Examiner—Howard W. Britton
Assistant Examiner—John K. Peng
Attorney, Agent, or Firm—Kane, Dalsimer, Sullivan, Kurucz, Levy, Eisele and Richard

[57] ABSTRACT

In an electronic endoscope apparatus, image signals from a solid state image pickup device are converted into television picture signals, and pictures are displayed on a monitor television on the basis of the television picture signals. At least one chopper is arranged between a light source and an end of an optical system for transmitting an illuminating light from the light source to an illuminating window of an endoscope. The chopper is rotated by a motor to bring the illuminating light into the form of pulses. Rotation of the chopper is controlled in such a manner that a center of supply time duration of each illuminating light pulse is brought into coincidence with a point of time at which the image signals to be offered to either one of odd and even field scannings are transferred from a light receiving portion to a memory portion of the image pickup device.

23 Claims, 19 Drawing Figures

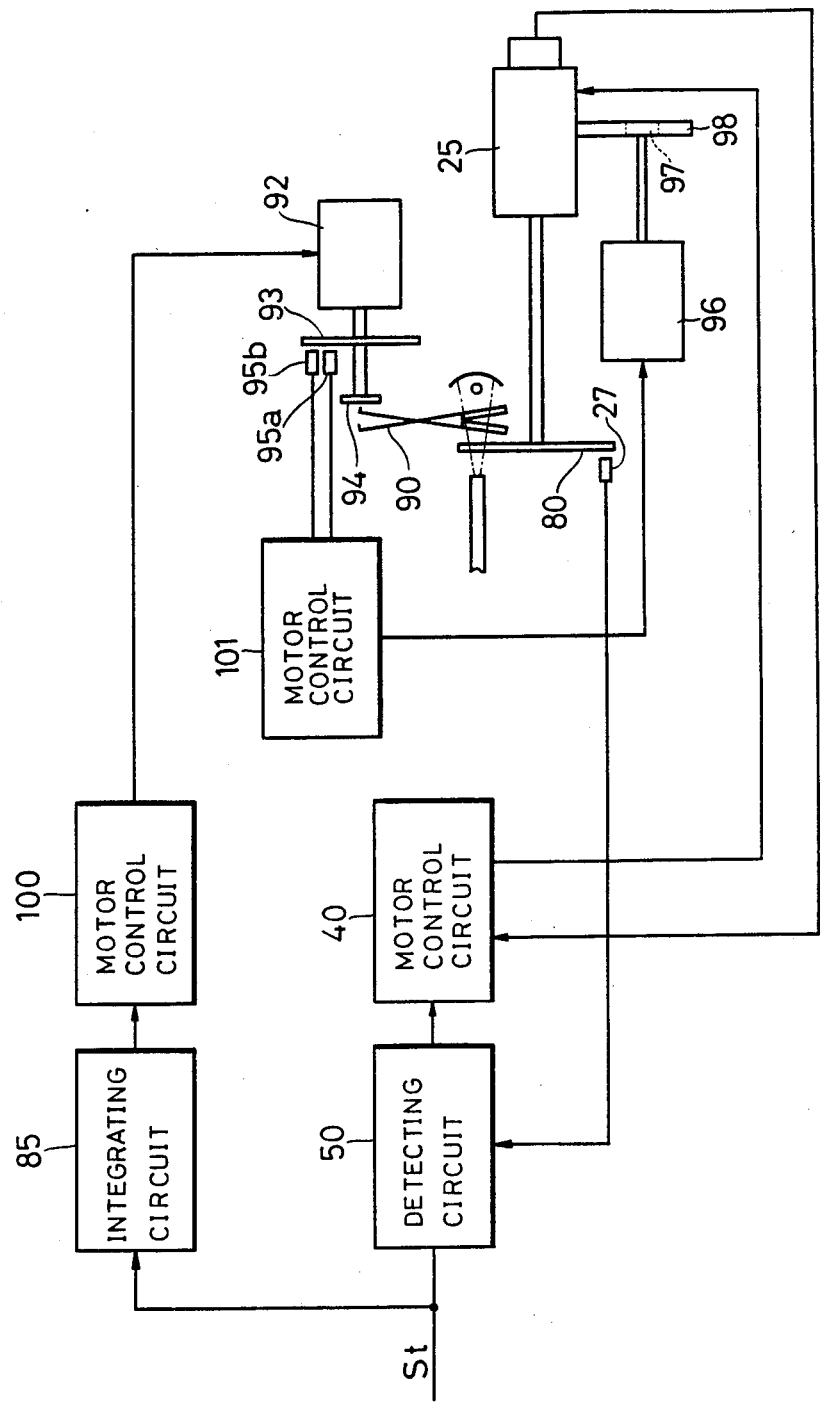

ILLUMINATING LIGHT SUPPLY SYSTEM IN ELECTRONIC ENDOSCOPE APPARATUS

BACKGROUND OF THE INVENTION

The present invention relates to an illuminating light supply system in an electronic endoscope apparatus in which an endoscope is connected to a monitor television.

A known electronic endoscope apparatus will be briefly described. An inserting portion of an endoscope is inserted into a subject to be inspected such as a body cavity of a patient, interior of machines, interior of piping or the like, for example. Illuminate-light is irradiated through an illuminating window provided at a distal end of the inserting portion. The light reflected from a wall surface of the body cavity enters through a viewing window provided at the distal end of the inserting portion, and is received by a light receiving portion of a solid state image pickup element such as CCD (charge coupled device) arranged within the distal end of the inserting portion and adjacent the viewing window. The light received by the image pickup element is photoelectrically converted into image signals. The image signals are converted into television picture signals by a picture circuit connected to the image pickup element, and the picture signals are supplied to a monitor television on which images of the interior of the body cavity are displayed.

More specifically, in the aforesaid monitor television, an interlaced scanning is performed similarly to general television machines, i.e., one frame scanning is performed by an odd field scanning and an even field scanning. Firstly, the horizontal scannings are coarsely performed by the odd field scanning, and then areas between pairs of adjacent horizontal scanning lines are horizontally scanned by the even field scanning.

A vertical synchronizing signal is generated by the picture circuit during a short blanking period between each pair of adjacent field scanning durations and, immediately thereafter, a transfer command signal is sent from the picture circuit to the image pickup element. In the image pickup element, in response to the transfer command signal, electric charge representative of the image signal of each of the picture elements obtained by the light receiving portion is transferred at a time to a memory portion of the image pickup element. The transfer time is very short and is on the order of 0.1 msec. The image signals to be offered to each field scanning are sent from the memory portion of the image pickup element to the picture circuit where the television picture signals for the odd and even field scannings are alternately outputted on the basis of the image signals.

When a precise diagnosis is required, a frame memory is utilized to store television picture signals corresponding to one frame scanning, and stationary pictures are projected on the monitor television on the basis of the stored television picture signals. This permits the stationary pictures to be viewed, recorded on an optical disc, or photographed by a camera.

However, the stationary pictures are not so much clear, and it is difficult to precisely conduct the diagnosis. The reasons for this will be discussed below.

The illuminating light is continuously irradiated into the body cavity through the illuminating window. Each picture element in the light receiving portion of the image pickup element continuously receives the reflected light for one field scanning duration (1/60 second), and the electirc charge corresponding to an integrated value of the amount of light received is stored in the memory portion of the image pickup element. Consequently, an amount of movement of the subject to be viewed during one field scanning time is stored as blur of the image, and the picture per se corresponding to one field scanning cannot have sufficient sharpness. This resembles, in principle, the relationship between opening time of a shutter and shapness of a photographed image of a camera. That is, in the camera, since the image information is continuously stored on a film for a time period during which the shutter is opened, should the opening time be long, the image of a subject to be photographed which is fast in movement would be blurred.

Furthermore, since the stationary picture projected on the monitor television is constituted by the overlap of the respective pictures due to two, i.e., odd and even field scannings, the amount of movement of the subject to be viewed corresponding to one frame scanning time (1/30 second) inevitably appears as blur.

OBJECT AND SUMMARY OF THE INVENTION

An object of the present invention is to provide an electronic endoscope apparatus which can obtain clear and sharp, in particular, stationary pictures on a monitor television, thereby making it possible to precisely observe a subject to be viewed.

According to the invention, there is provided an electronic endoscope apparatus comprising:

(a) an endoscope including an operating body, an inserting portion extending from the operating body, and a viewing window and an illuminating window provided at respective appropriate locations of the inserting portion;

(b) a solid state image pickup device including a light receiving portion for receiving images entering through the viewing window of the endoscope, and a memory portion for storing image signals from the light receiving portion;

(c) circuit means for converting the image signals from the image pickup device into television picture signals of an interlaced scanning system;

(d) a monitor television for displaying pictures on the basis of the television picture signals;

(e) light source means;

(f) an illuminating light transmitting optical system arranged within the endoscope, for transmitting an illuminating light from the light source means to the illuminating window;

(g) chopper means disposed between an end of the illuminating light transmitting optical system and the light source means and including at least one light shielding section and at least one light transmitting section;

(h) motor means for rotating the chopper means to cause the light shielding section and the light transmitting section of the chopper means to successively cross a luminous flux of the illuminating light, to thereby bring the illuminating light into the form of pulses; and (i) synchronizing circuit means for controlling the rotation of the motor means in such a manner that a center of supply time duration of each of the illuminating light pulses is brought into coincidence with a point of time at which the image signals to be offered to either one of odd and even field scannings are transferred from the light receiving portion to the memory portion of the image pickup device.

BRIEF DESCRIPTION OF THE DRAWINGS

FIG. 19 is a block diagram showing an electric circuit for controlling the chopper and the shielding members shown in FIGS. 17 and 18.

DETAILED DESCRIPTION

Figure 1:
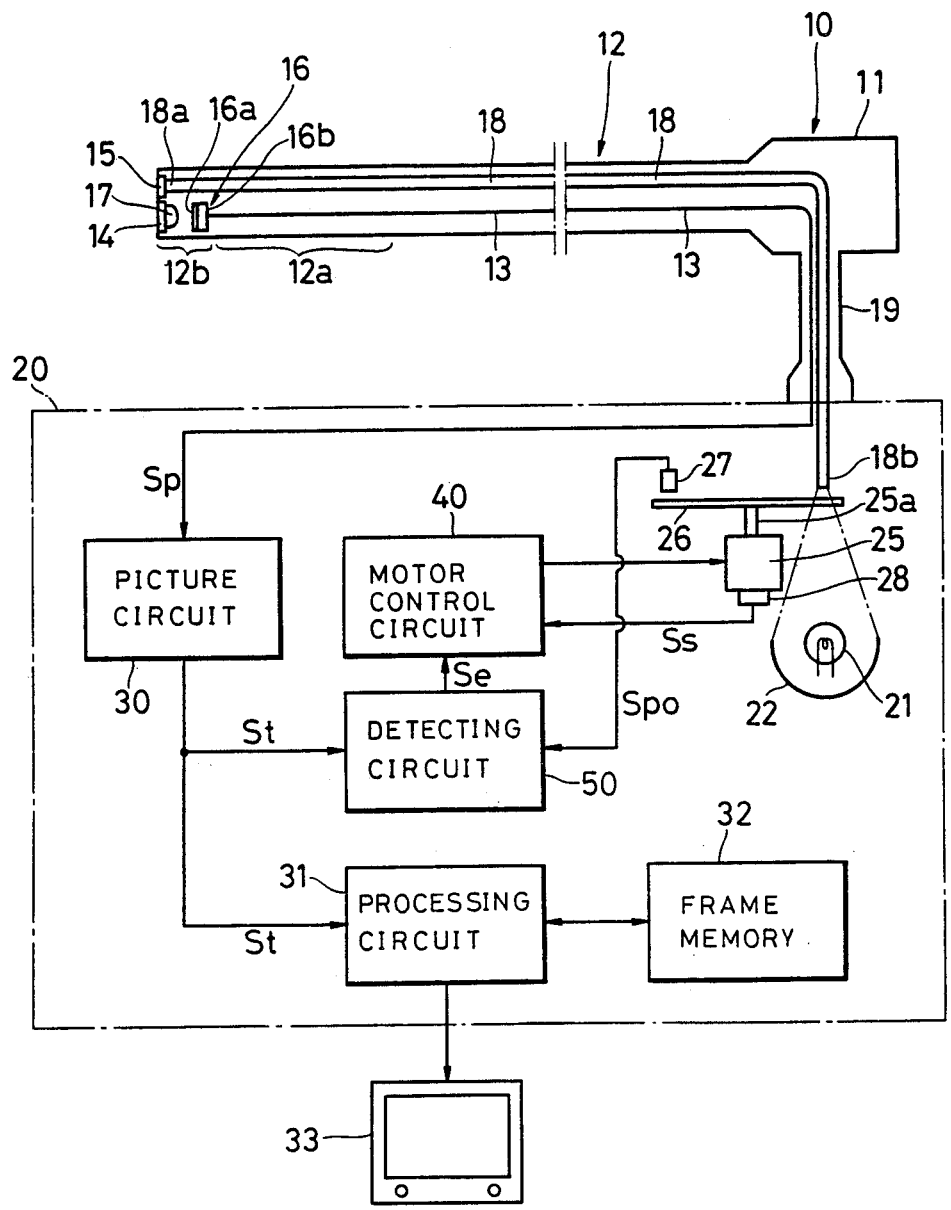
FIG. 1 is a diagrammatic view showing an electronic endoscope apparatus according to a first embodiment of the invention, with an electric circuit shown in a block diagram.

Various embodiments of the invention will now be described with reference to the accompanying drawings in which like reference numerals and characters are used to designate like or similar parts and components.

Referring to FIGS. 1 through 5, in particular, to FIG. 1, an electronic endoscope apparatus in accordance with a first embodiment of the invention comprises an endoscope generally designated by the reference numeral 10. The endoscope 10 includes an operating body 11 having no ocular portion, and an elongated, flexible inserting portion 12 extending from a front end of the operating body 11. A distal end section of the inserting portion 12 is formed into a bendable section 12a which is capable of being bent by remoteoperation of an operating lever or the like (not shown) at the operating body 11. The bendable section 12a has at its distal end a hard or rigid tip component 12b which is provided in an end face thereof with a viewing window 14 and an illuminating window 15. A solid state image pickup element 16 such as CCD (charge coupled device) is arranged within the tip component 12b. The image pickup element 16 is known per se and is schematically illustrated in FIG. 1. The image pickup element 16 has a light receiving portion 16a optically connected to the viewing window 14 through a convex lens 17, and a memory portion 16b electrically connected to the light receiving portion 16a. The image pickup element 16 has connected thereto a multiplicity of signal lines 13 only one of which is illustrated in FIG. 1. The illuminating window 15 is optically connected to one end 18a of an optical fiber bundle 18.

The operating body 11 has a lower surface thereof to which one end of a cable 19 is connected. The other end of the cable 19 is connected to a box 20. The optical fiber bundle 18 and the signal lines 13 pass through the inserting portion 12, operating body 11 and cable 19, and extends into the box 20.

The box 20 contains a light bulb 21 serving as a light source, which is mounted at a center of a shade 22 formed by a concave mirror. Thus, the light from the bulb 21 is reflected and condensed by the shade 22 and is supplied to the other end 18b of the optical fiber bundle 18.

Figure 3:
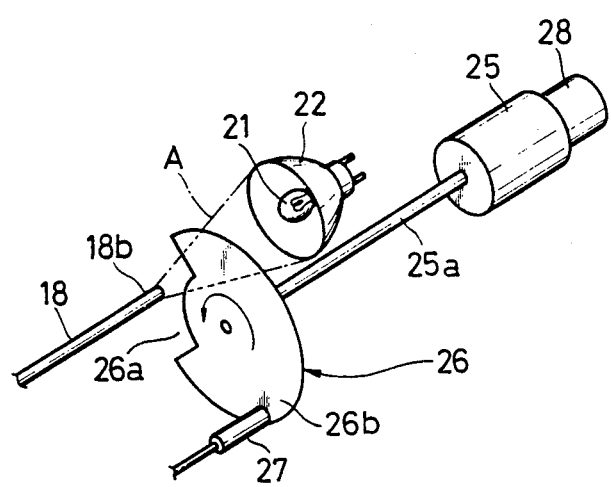
FIG. 3 is a perspective view showing a chopper control mechanism for use in the electronic endoscope apparatus shown in FIG. 1.
Figure 4:
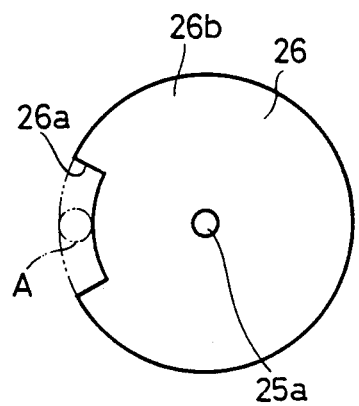
FIG. 4 is a diagrammatic front elevational view showing a positional relationship between a chopper and luminous flux of illuminating light shown in FIG. 3.

The box 20 also contains an electric motor 25 having an output shaft 25a on which a chopper 26 in the form of a disc is concentrically mounted for rotation with the output shaft 25a, as shown in detail in FIG. 3. The chopper 26 has a circumferential portion thereof from which an arcuate section extending through a predetermined angular extent is cut to form an arcuate window 26a, and the remaining section of the circumferential portion forms a shielding section 26b. As shown in FIG. 4, a luminous flux A of the illuminating light supplied from the bulb 21 to the end 18b of the optical fiber bundle 18 extends across the rotational locus of the window 26a and the shielding section 26b of the chopper 26 when rotated by the motor 25. A position sensor 27 is arranged in the vicinity of the chopper 26, for detecting a position of a specific location on the chopper 26, e.g. one of longitudinal end edges ofthe window 26a in the illustrated embodiment. The position sensor 27 may, for example, be a photosensor having a light emitting portion and a light receiving portion.

Moreover, a speed sensor 28 such as a tachogenerator is mounted on the motor 25, for detecting the rotational speed thereof.

As shown in FIG. 1, a picture circuit 30 is incorporated into the box 20 and is connected to the image pickup element 16 through the signal lines 13. The picture circuit 30 is also connected to a frame memory 32 and to a monitor television 33 through a processing circuit 31. The monitor television 33 is arranged exteriorly of the box 20. These picture circuit 30, processing circuit 31, frame memory 32 and monitor television 33 are known per se, and the description of such components will therefore be omitted.

The box 20 also contains a motor control circuit 40 and a detecting circuit 50. The detecting circuit 50 receives television picture signals St from the picture circuit 30 and detected position signals from the position sensor 27, and outputs deviation siganls Se to the motor control circuit 40. The motor control circuit 40 receives the deviation signals Se from the detecting circuit 50 and speed signals Ss from the speed sensor 28 to control the rotational speed of the motor 25.

Figure 2:
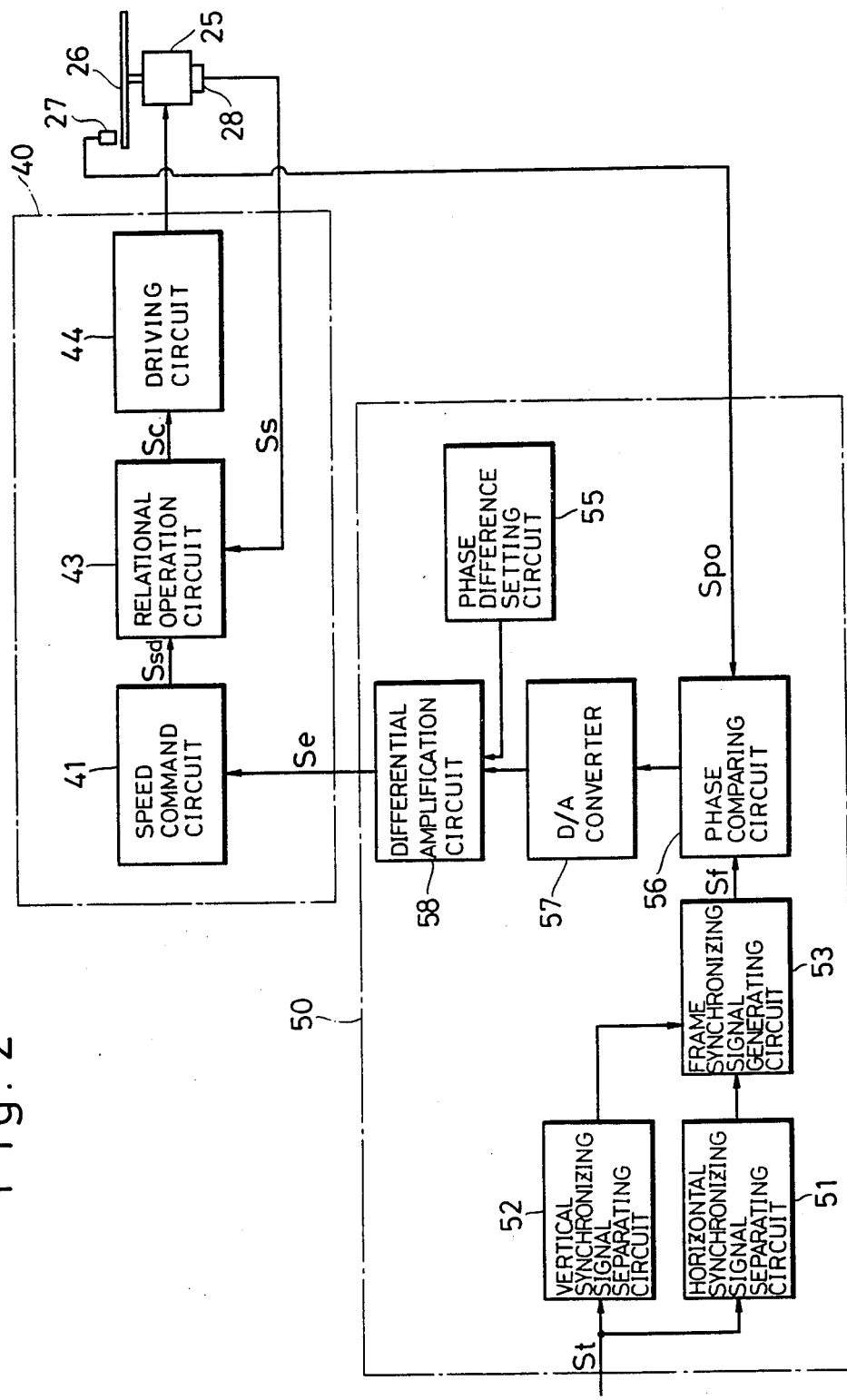
FIG. 2 is a block diagram of the electric circuit incorporated into the electronic endoscope apparatus shown in FIG. 1.

As shown in FIG. 2, the motor control circuit 40 includes a speed command circuit 41, a relational operation circuit 43 and a driving circuit 44.

The detecting circuit 50 includes a horizontal synchronizing signal separating circuit 51, a vertical synchronizing signal separating circuit 52, a frame synchronizing signal generating circuit 53, a phase comparing circuit 56, a D/A converter 57, a phase difference setting circuit 55 and a differential amplification circuit 58.

The operation of the electronic endoscope apparatus constructed as described above will be described. An operating surgeon holds, with his hand, the operating body 11 of the endoscope 10, and inserts the inserting portion 12 into the body cavity of the subject, for example, from the mouth into the stomach. The light from the bulb 21 within the box 20 passes through the optical fiber bundle 18 and is irradiated into the body cavity through the illuminating window 15. The light reflected from the inner wall of the body cavity passes through the viewing window 14 and the convex lens 17 and reaches the solid state image pickup element 16. As a result, the image representative of the inner wall of the body cavity is focused on the light receiving portion 16a of the image pickup element 16. The light receiving portion 16 photoelectrically converts the projected image into image signals and stores the same as electric charges.

The picture circuit 30 generates a vertical synchronizing signal within a short blanking period between each pair of adjacent field scanning durations and, immediately thereafter, generates a transfer command signal such as clock pulse. In the image pickup element 16, the electric charges corresponding to one filed scanning are transferred from the light receiving portion 16a to the memory portion 16b within a short period of time (0.1 msec) in response to the transfer command signal. The picture circuit 30 successively receives the image signals from the memory portion 16a of the image pickup element 16, converts the image signals into NTSC (National Television System Committe) television picture signals St, and sends the same to the monitor television 33. As a result, the pictures representative of the inner wall of the body cavity are projected on the monitor television 33 in an interlaced scanning manner.

The operating surgeon operates the endoscope 10 while watching the monitor television 33, to observe the interior of the body cavity. When precise inspection is required, the television picture signals St corresponding to one frame scanning (corresponding to one odd field scanning and one even filed scanning) are stored in the frame memory 32 in response to the command or instructions from the processing circuit 31. The stored signals are repeatedly read out by the processing circuit 31 and are sent to the monitor television 33, so that stationary pictures are projected on the monitor television 33.

The stationary pictures are rendered clear and sharp by the intermittent supply of the illuminating light due to the rotation of the chopper 26, and the operation thereof will be described below.

The motor 25 is driven to rotate the chopper 26. The chopper 26 is rotated by one revolution per one frame scanning duration. During the period within which the shielding section 26b of the chopper 26 shields the luminous flux A of the illuminating light, the body cavity is not supplied with the illuminating light from the illuminating window 15. The body cavity is supplied with the illuminating light only when the window 26a of the chopper 26 is located at the luminous flux A. As a result, the illuminating light is brought into the form of pulses and is intermittently supplied into the body cavity.

In each field scanning duration, the light receiving portion 16a of the image pickup element 16 does not store the electric charges, i.e., image signals during the dark view when the illuminating light is not supplied into the body cavity, but stores the electric charges corresponding to the amount of light received only for the period of time during which the illuminating light is supplied. In addition, as will be described later, the illuminating light pulses are supplied in such a manner that each pulse straddles a corresponding one of the transfer points of time of the image signals to be offered to the odd field scanning. For this reason, the accumulating duration of the image signals to be offered to the odd field scanning, i.e., the time duration during which the illuminating light is supplied, is continuous to the accumulating duration of the image signals to be offered to the subsequent even field scanning, i.e., the time duration during which the illuminating light is supplied. As a result, the stationary picture, corresponding to one frame scanning, projected on the monitor television 33 is formed by the overlap of two pictures (each corresponding to one field scanning) each accumulated during the half of the continuous time duration.

As described above, the stationary picture is based on the picture signals accumulated during the supply time duration of the illuminating light, and is low in blur as compared with a picture based on picture signals accumulated during the whole duration of one frame scanning as is in the prior art described previously, so that the stationary picture can be made clear and sharp, even when the subject to be observed is fast in movement. This phenomenon corresponds to the case where time duration during which a shutter of a camera is opened is shortened.

Figure 5:
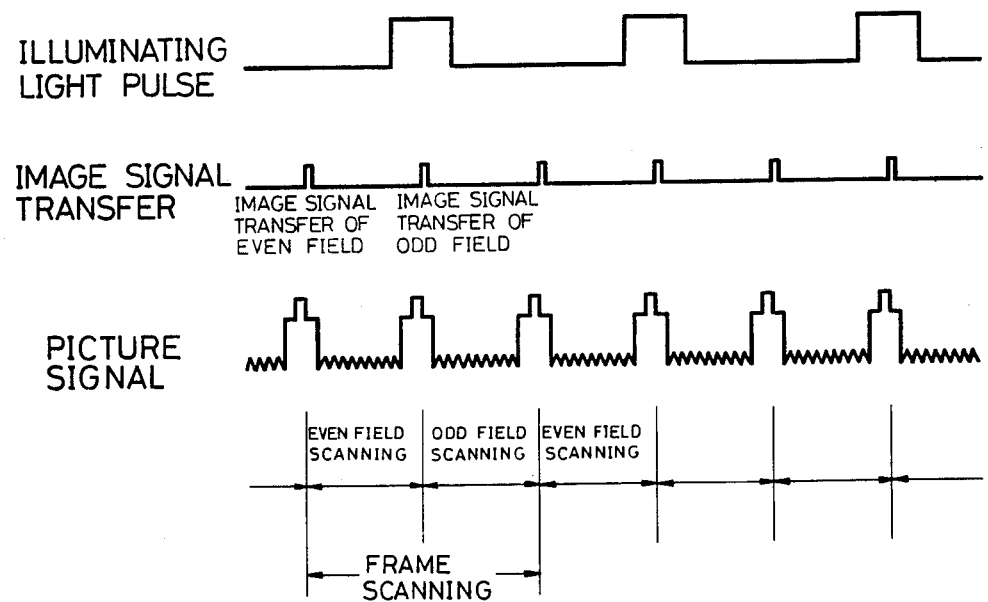
FIG. 5 is a time chart showing a timing at which the illuminating light pulses are supplied, in the electronic endoscope apparatus shown in FIG. 1.

Moreover, as shown in FIG. 5, the rotation of the chopper 26 is controlled such that the center of the supply time duration of each of the illuminating light pulses is coincident with the corresponding point of time at which the image signals to be offered to the odd field scanning are transferred from the light receiving portion 16a to the memory portion 16b of the image pickup element 16.

Specifically, when the motor 25 is driven to rotate the chopper 26 while light is illuminated from the position sensor 27 onto the chopper 26, the position sensor 27 differentiates the voltage obtained by the photoelectric conversion of the light reflected from the chopper 26. Abrupt increase in the amount of light reflected occurs when one of the longitudinal end edges of the window 26a crosses the position sensor 27. The sensor 27 detects a pulse generated at this time and outputs detected position signal Spo.

On the other hand, in the detecting circuit 50, as shown in FIG. 2, the television picture signals St are supplied to the horizontal synchronizing signal separating circuit 51 and the vertical synchronizing signal separating circuit 52. The circuit 51 separates horizontal synchronizing signals and equalizing signals from the television picture signals St and outputs these signals to the frame synchronizing signal generating circuit 53. The circuit 53 discriminates the odd and even field scannings on the basis of the time difference between the last horizontal synchronizing signal of each field scanning duration received from the horizontal synchronizing signal separating circuit 51, and the subsequent equalizing signal, and outputs the frame synchronizing signal Sf when the circuit 53 receives one of the vertical synchronizing signals sent twice from the circuit 52 every frame scanning, for example, the vertical synchronizing signal for the odd field scanning. As a result, the circuit 53 outputs the frame synchronizing signal Sf once per each frame scanning.

The phase difference detecting circuit 56 compares the frame synchronizing signal Sf from the circuit 53 with the detected position signal Spo from the position sensor 27, to detect a phase difference therebetween which is converted by the D/A converter into an analog phase difference signal which, in turn, is outputted to the differential amplification circuit 58. The circuit 58 compares the phase difference signal with an analog, set phase difference signal from the phase difference setting circuit 55, and outputs a deviation signal Se. The phase difference set by the circuit 55 is determined depending upon the difference between first and second time durations. The first time duration is from the time when the position sensor 27 detects longitudinal one end edge of the window 26a in the chopper 26 to the time when the longitudinal center of the window 26a reaches the center of the luminous flux A. The second time duration is from the point of time at which the frame synchronizing signal Sf is generated to the transfer point of time at which the image signals are transferred from the light receiving portion 16a to the memory portion 16b of the image pickup element 16. Accordingly, the deviation signal Se represents the phase difference between the transfer point of time and the point of time when the center of the window 26a reaches the center of the luminous flux A, in other words, the point of time corresponding to the center of the duration during which the illuminating light is supplied. Incidentally, it is possible to finely adjust the aforesaid set phase difference manually by means of a dial or the like.

The speed command circuit 41 of the motor control circuit 40 receives the deviation signal Se, adds the deviation to a speed value set previously, and outputs a speed command signal Ssd. The relational operation circuit 43 compares the speed command signal Ssd with a detected speed signal Ss from the speed sensor 28 and outputs a control signal Sc to the driving circuit 44 so as to eliminate the deviation between the signals Ssd and Ss. The driving circuit 44 is operative in response to the control signal Sc to increase or decrease the electric power supplied to the motor 25, to thereby control the rotational speed of the chopper 26.

As described above, since the rotation of the chopper 26 is automatically controlled so as to eliminate the deviation signal Se, it is possible to bring the point of time at which the center of the window 26a in the chopper 26 crosses the center of the luminous flux A, into coincidence with the transfer point of time of the image signals to be offered to the odd field scanning, so that the center of the time duration during which each of the illuminating pulses is supplied can be brought into coincidence with the point of time at which the image signals are transferred.

Thus, the illuminating light pulse width in the image signal accumulating duration by the image pickup element for the odd field scanning is made equal to that in the image signal accumulating duration by the image pickup element for the even field scanning. Consequently, the picture projected on the monitor television is minimized in flicker, and the stationary picture can have good quality and the colors can also be accurately reproduced.

Figure 6:
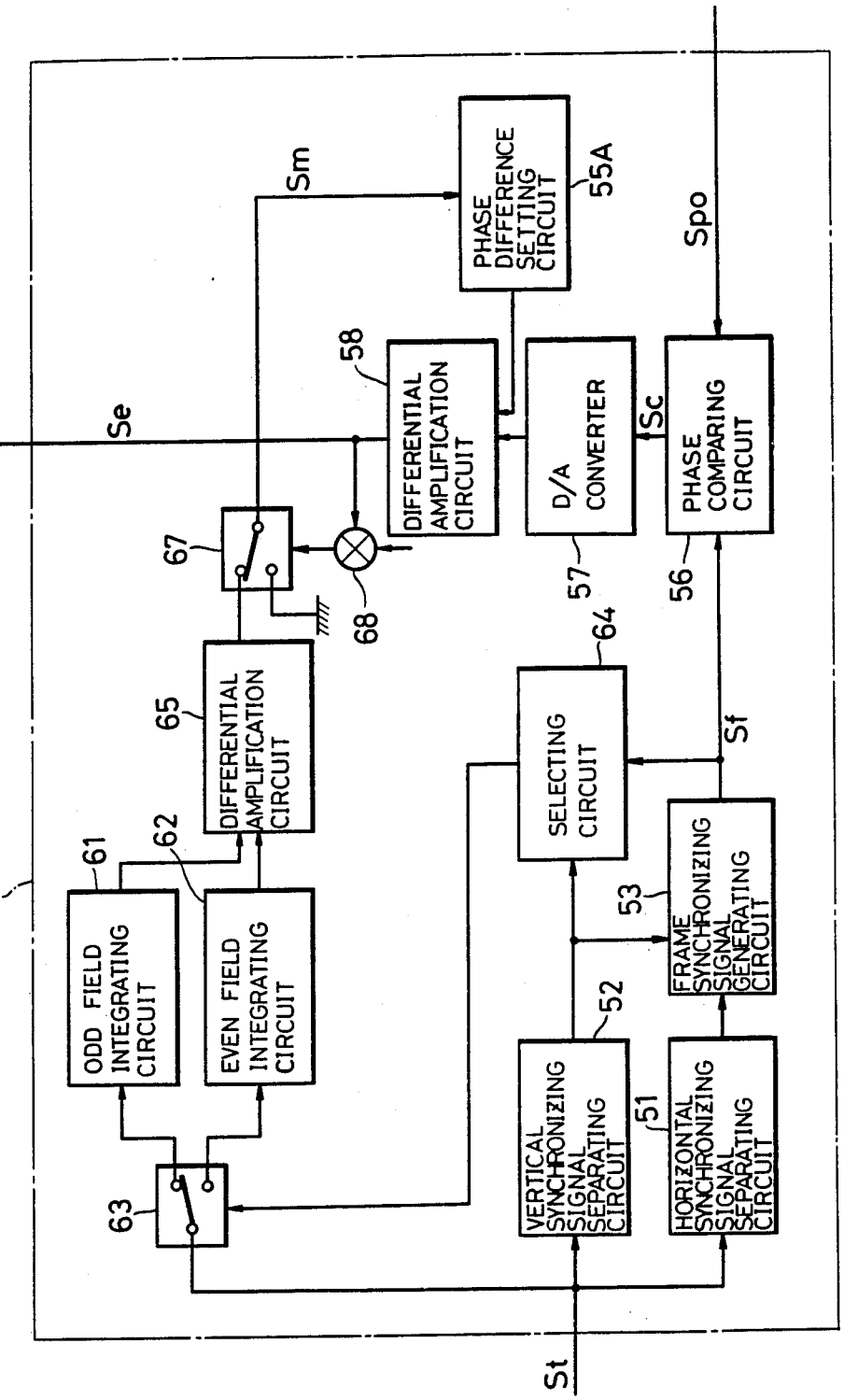
FIGS. 6 to 8 are block diagrams showing detecting circuits incorporated respectively into second to fourth embodiments of the invention.

FIG. 6 shows a second embodiment of the invention into which a detecting circuit 60 is incorporated in substitution for the detecting circuit 50 in the first embodiment described previously with reference to FIGS. 1 through 4. In FIG. 6, the same reference numerals and characters are used to designate parts and components like or similar to those shown in FIGS. 1 through 4, and the description of such like or similar parts and components will therefore be omitted. The detecting circuit 60 in the second embodiment can automatically finely adjust the aforesaid set phase difference in such a manner that the picture of the odd field scanning is made equal in brightness to the picture of the even field scanning.

Specifically, the detecting circuit 60 includes an odd field integrating circuit 61 for integrating the television picture signals St for the odd field scanning to detect the brightness thereof, and an even field integrating circuit 62 for integrating the television picture signals St for the even field scanning to detect the brightness thereof. The integrating circuits 61 and 62 are connected to the picture circuit 30 (FIG. 1) through a selector 63, so that the television picture signals St are distributed to the integrating circuits 61 and 62 by the selector 63 every field scanning. The selector 63 is actuated by instructions from a selecting circuit 64 which discriminates a case where the selecting circuit 64 receives only the vertical synchronizing signals from the vertical synchronizing signal separating circuit 52, and a case where the selecting circuit 64 simultaneously receives the vertical synchronizing signals and the frame synchronizing signals Sf from the frame synchronizing signal generating circuit 53, to output the selecting command signal to the selector 63. The brightness signals outputted respectively from the integrating circuits 61 and 62 are supplied to a differential amplification circuit 65 which compares the brightness signals with each other to output a brightness difference signal Sm to a phase difference setting circuit 55A. The circuit 55A finely adjusts the set phase difference on the basis of the brightness difference signal Sm, and outputs the finely adjusted, set phase difference signal to the differential amplification circuit 58.

In the second embodiment shown in FIG. 6, at the initial stage of the driving of the motor 25, the time duration during which the chopper 26 is rotated by one revolution is considerably different from the time duration of one frame scanning, and the difference in brightness between the respective pictures due to the odd and even field scannings is considerably great. This makes it impossible to finely adjust the set phase difference on the basis of the brightness difference. For this reason, the following measures are taken into consideration. That is, a selector 67 is interposed between the differential amplification circuit 65 and the phase difference setting circuit 55A. The selector 67 interrupts the connection between the differential amplification circuit 65 and the phase difference setting circuit 55A at the initial stage of the driving of the motor 25, and the phase difference setting circuit 55A outputs the phase difference signal set previously to the differential amplification circuit 58. Similarly to the first embodiment illustrated in FIGS. 1 through 4, the circuit 58 outputs the deviation signal Se to the speed command circuit 41

(FIG. 2), and also to a comparator 68. The comparator 68 compares the deviation signal Se with a set value, and sends a selecting command signal to the selector 67 when the deviation reaches a level lower than the set value, to thereby actuate the selector 67 so as to permit the differential amplification circuit 65 to be connected to the phase difference setting circuit 55A. Subsequently, the set phase difference is finely adjusted in accordance with the aforementioned brightness difference.

Figure 7:
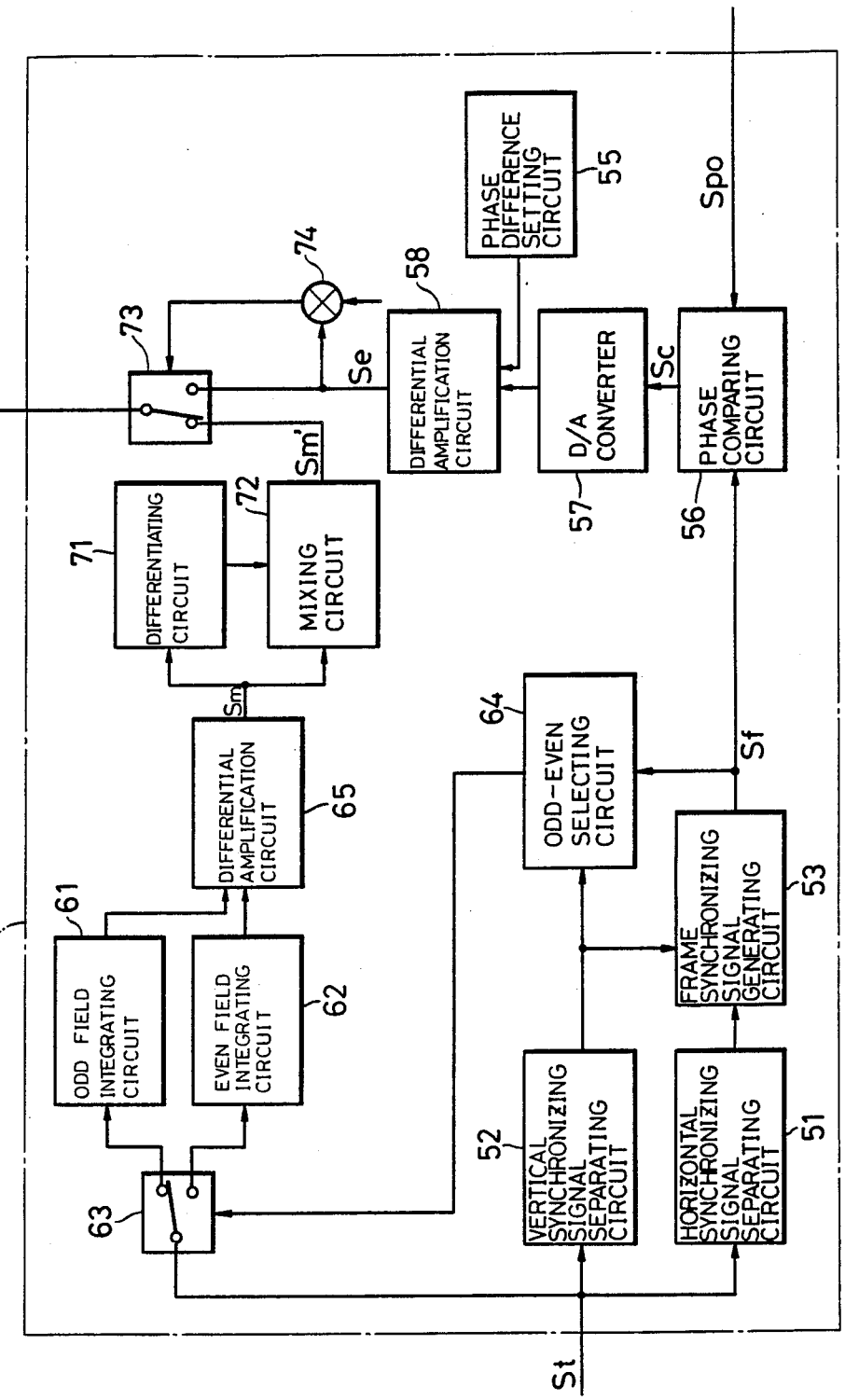

FIG. 7 shows a third embodiment of the invention. A detecting circuit 70 in the third embodiment is similar to that in the second embodiment shown in FIG. 6 in that the detecting circuit 70 detects phase difference and brightness difference. However, a signal of the brightness difference is not supplied to the phase difference setting circuit 55, and the fine adjustment of the set phase difference is not performed. Alternatively, the signal of the brightness difference is sent to the speed command circuit 41 (FIG. 2) and is offered to the control of the rotation of the motor 25 (FIG. 2).

At the initial stage of the driving of the motor 25, the time duration during which the chopper 26 is rotated by one revolution is considerably different from the time duration of one frame scanning, and the difference in brightness between the respective pictures of the odd and even field scannings is very great. For this reason, it is difficult to control the motor 25 on the basis of the brightness difference. Consequently, similarly to the first embodiment shown in FIGS. 1 through 4, at the transient stage immediately after the start of the driving of the motor 25, the deviation signal Se is sent to the speed command circuit 41 (FIG. 2), and the rotation of the motor 25 is controlled on the basis of the deviation signal Se.

During the stable stage, the motor 25 is controlled on the basis of the brightness difference between the odd and even fields. Specifically, the brightness difference signal Sm from the differential amplification circuit 65 is sent to a differentiating circuit 71 and a mixing circuit 72. The circuit 71 differentiates the brightness difference signal Sm. The mixing circuit 72 adds the differentiating signal from the circuit 71 to the brightness difference signal Sm, to obtain an analog, modified brightness difference signal Sm', and outputs the signal Sm' to the speed command circuit 41 (FIG. 2) of the motor control circuit 40. The circuit 40 controls the rotation of the motor 25 on the basis of the modified brightness difference signal Sm'. Incidentally, since the differentiated value of the brightness difference signal Sm is contained in the modified brightness difference signal Sm', it is possible to perform sensitive control.

As described above, the automatic control of the chopper 26 on the basis of the brightness difference between the odd and even field scannings makes it possible to always divide each illuminating light pulse accurately into two halves with the boundary of the aforesaid transfer point of time. As a result, the picture projected on the monitor television is minimized in flicker, and has good quality, and the colors can be accurately reproduced.

The switching-over from the chopper control due to the phase difference at the transient stage to the chopper control due to the brightness difference during the stable stage is performed by a selector 73. Specifically, the deviation signal Se from the differential amplification circuit 58 is compared with a set value by a comparator 74. When the comparison indicates that the deviation signal Se is higher than the set value, the selector 73 allows the differentiate amplification circuit 58 to be connected to the speed command circuit 41 (FIG. 2). When the comparison indicates that the deviation signal Se is lower than the set value, the selector 73 is switched-over to allow the mixing circuit 72 to be connected to the speed command circuit 41.

Figure 8:
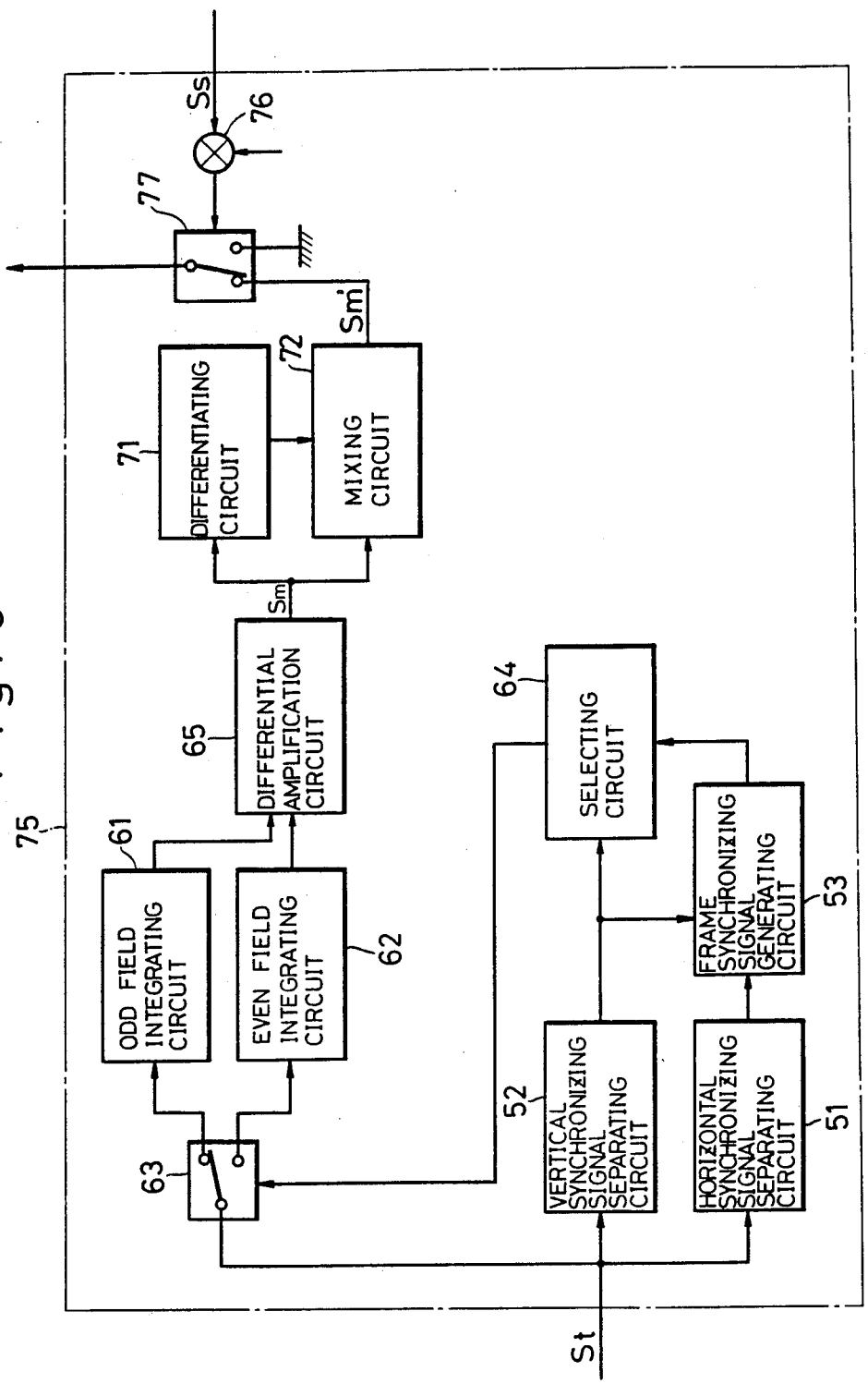

FIG. 8 shows a fourth embodiment of the invention in which a detecting circuit 75 is similar to that in the third embodiment illustrated in FIG. 7, but does not perform the phase difference detection. Accordingly, it is unnecessary for the fourth embodiment to have the position sensor 27 shown in FIG. 1. Specifically, the detected speed signal Ss from the speed sensor 28 (FIG. 1) is sent to a comparator 76 which compares the detected speed signal Ss with a set value. If the comparison indicates that the detected speed signal Ss is lower than the set value, the connection between the mixing circuit 72 and the speed command circuit 41 (FIG. 2) is interrupted by a selector 77. Thus, at the initial stage of the driving of the motor 25, the control based on the brightness difference is not performed, but the rotation of the motor 25 is controlled on the basis of the set speed signal determined previously by the speed command circuit 41. As the rotational speed of the motor 25 increases gradually and the detected speed signal Ss exceeds the set value, the selector 77 is switched-over in response to the switching-over signal from the comparator 76, to connect the mixing circuit 72 to the speed command circuit 41, to thereby initiate the control based on the brightness difference.

Figure 9:
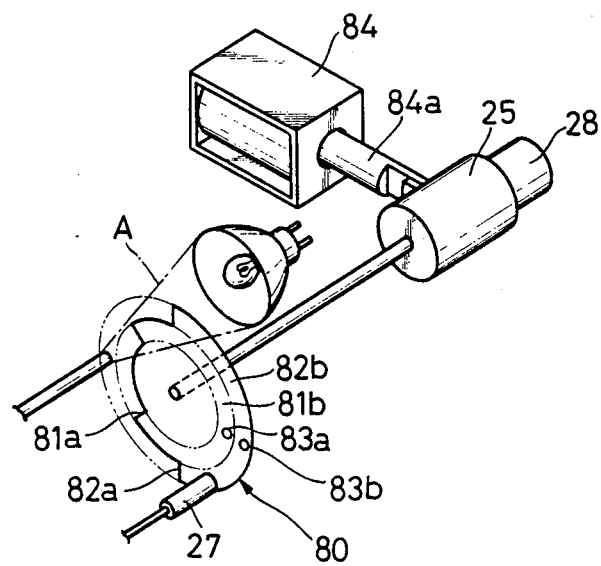
FIG. 9 is a perspective view showing a chopper control mechanism for use in a fifth embodiment of the invention.

FIGS. 9 through 12 show a fifth embodiment of the invention which can adjust, in two steps, the time duration during which each illuminating light pulse is supplied. As shown in FIG. 9, a chopper 80 is formed therein with first and second arcuate windows 81a and 82a angularly extending around a common axis and arranged in side by side relation. Specifically, an arcuate section extending through a relatively wide angular extent, e.g., through 180 degrees is cut from an outer circumferential portion of the chopper 80 to form the second window 82a, and the remaining section of the outer circumferential portion is formed into a second shielding section 82b having the same radius of curvature as the second window 82a. An arcuate section is cut from a circumferential portion of the chopper 80 which is shifted radially inwardly from the outer circumferential portion, to form the first window 81a, and the remaining section of the circumferential portion is formed into a first shielding section 81b having the same radius of curvature as the first window 81a. The first window 81a has its angular extent which is smaller than that of the second window 82a and which is 90 degrees, for example. The chopper 80 has its surface which is not reflective, but reflective spots 83a and 83b are formed respectively at specific locations on the respective first and second shielding sections 81b and 82b. The arrangement is such that either one of the reflective spots 83a and 83b is detected by the position sensor 27.

The motor 25 and the chopper 80 are adapted to be shifted in the direction perpendicular to the optical axis of the luminous flux A of the illuminating light, by means of a shifter 84 which comprises a solenoid (not shown) and a rod 84a having a tip end connected to the motor 25. When the solenoid of the shifter 84 is energized, the magnetic force of the solenoid causes the rod 84a to be retracted, and when the solenoid is deenergized, the rod 84a is projected by a return spring (not shown).

Figure 10:
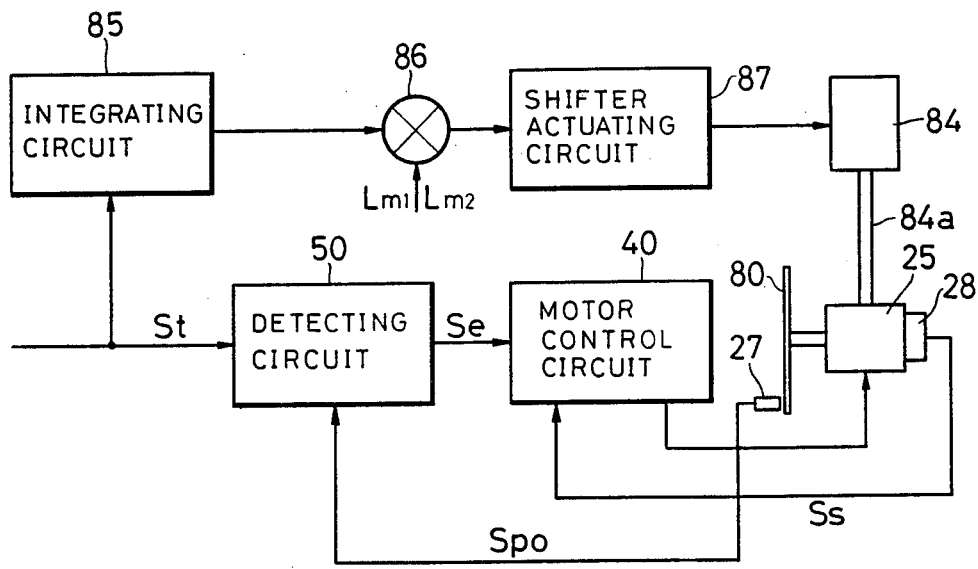
FIG. 10 is a block diagram showing an electric cirouit incorporated into the chopper control mechanism shown in FIG. 9.

The rotation of the chopper 80 is controlled in the same manner as the first embodiment shown in FIG. 1 through 4. That is, as shown in FIG. 10, the control system comprises the detecting circuit 50 and the motor control circuit 40. The detecting circuit 50 receives the television picture signals St from the picture circuit 30 (FIG. 1) and the detected position signals Spo from the position sensor 27, and outputs the deviation signals Se therebetween to the motor control circuit 40. The circuit 40 receives the deviation signal Se from the detecting circuit 50 and the detected speed signal Ss from the speed sensor 28, to control the rotational speed of the chopper 26.

An integrating circuit 85 is connected to the picture circuit 30 (FIG. 1), and a shifter actuating circuit 87 is connected to the integrating circuit 85 through a comparator 86 having a hysteresis characteristic. The shifter 84 is actuated and controlled by the shifter actuating circuit 87.

Figure 11:
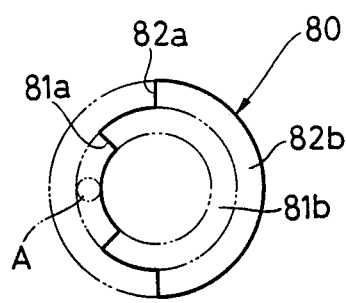
FIG. 11 and 12 are front elevational views respectively showing different positional relationships between the chopper and luminous flux shown in FIG. 9.

In the fifth embodiment shown in FIGS. 9 through 12, the time duration during which each illuminating light pulse is supplied is controlled in two steps by changing the position of the chopper 80 with respect to the luminous flux A by the shifter 84. The first step of the illuminating light supply will first be described. In FIG. 9, when the solenoid of the shifter 84 is energized to retract the rod 84a, the motor 25 and the chopper 80 are moved to the left as viewed in FIG. 9. This results in the positional relationship of the chopper 80 to the luminous flux A as shown in FIG. 11. In this positional relationship, the luminous flux A is located on the rotational locus of the first window 81a and first shielding section 81b of the chopper 80. Since the first window 81a has the angular extent which is relatively narrow, i.e., 90 degrees, the supply time duration of each illuminating light pulse is shortened.

Figure 12:
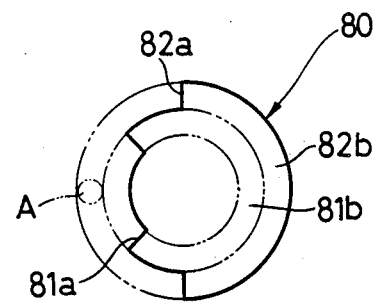

The second step of the illuminating light supply will next be described. When the solenoid of the shifter 84 is deenergized to permit the rod 84a to be projected, the motor 25 and the chopper 80 are moved to the right as viewed in FIG. 9. This results in the positional relationship of the chopper 80 to the luminous flux A as shown in FIG. 12. In this positional relationship, the luminous flux A is located on the rotational locus of the second window 82a and second shielding section 82b of the chopper 80. Since the second window 82a has the angular extent which is relatively wide, i.e., 180 degrees, the supply time duration of the illuminating light is lengthened.

The supply time duration of each illuminating light pulse is adjusted on the basis of the brightness of the picture which varies depending upon locations to be observed by the endoscope and used manners thereof. In the below discussion, the brightness levels (voltage levels) have the relation of $Lm_1 > Lm_2$. The picture signals St from the picture circuit 30 (FIG. 1) are integrated by the integrating circuit 85, correspondingly to one frame scanning, to detect the brightness of the picture. The brightness signal from the integrating circuit 85 is sent to the comparator 86. As the level of the brightness signal rises and exceeds the brightness level $Lm_1$, the actuating signal is outputted from the comparator 86 to the shifter actuating circuit 87 and, in response thereto, the shifter actuating circuit 87 supplies the electric power to the solenoid of the shifter 84. This results in the change of the chopper 80 from the position shown in FIG. 12 to the position shown in FIG. 11. Thus, the supply time duration of each illuminating light pulse is shortened.

Immediately thereafter, the level of the brightness signal sent from the integrating circuit 85 to the comparator 86 is also lowered to a level lower than the brightness level $Lm_1$. However, since the comparator 86 has the hysteresis characteristic, it does not supply the return signal to the shifter actuating circuit 87 until the level of the brightness signal is lowered to a level lower than the brightness level $Lm_2$.

The shift to the positional relationship shown in FIG. 11, i.e., the first step of the illuminating light supply is carried into practice when the illuminating efficiency is high, e.g., when the observation is done in close relation to the subject. The reason for this is that the percentage of the reflected amount of light entering through the viewing window with respect to the illuminating light irradiated through the illuminating window is high and, therefore, the brightness level of the picture signal is raised. By this shift, the brightness level is made appropriate, and it is made possible to prevent the picture on the monitor television 33 (FIG. 1) from being rendered dazzling.

As the brightness signal is lowered to a level lower than the brightness level $Lm_2$ when the first step of the illuminating light supply is carried out, the return signal is sent from the comparator 86 to the shifter actuating circuit 87. This results in deenergization of the solenoid of the shifter 84, and the chopper 80 is shifted to the positional relationship shown in FIG. 12. Thus, the supply time duration of the illuminating light is lengthened.

The shift to the positional relationship shown in FIG. 12, i.e., the second step of the illuminating light supply is carried into practice when the illuminating efficiency is low, e.g., when the observation is done in remote relation to the subject. The reason for this is that the percentage of the reflected amount of light entering through the viewing window with respect to the illuminating light irradiated through the illuminating window is low and, therefore, the brightness level of the picture signals is lowered. By this shift, the brightness level is made appropriate, and it is made possible to prevent the picture on the monitor television 33 from being rendered dark.

In this manner, the supply time duration of each illuminating light pulse is switched-over depending upon the illuminating efficiency, and the illuminated amount of light offered to one field scanning duration is adjusted. Consequently, in the normally used manner, it is possible to bring the brightness signal level to a level between $Lm_1$ and $Lm_2$, and this makes appropriate the brightness of the picture projected on the monitor television 33.

Figure 13:
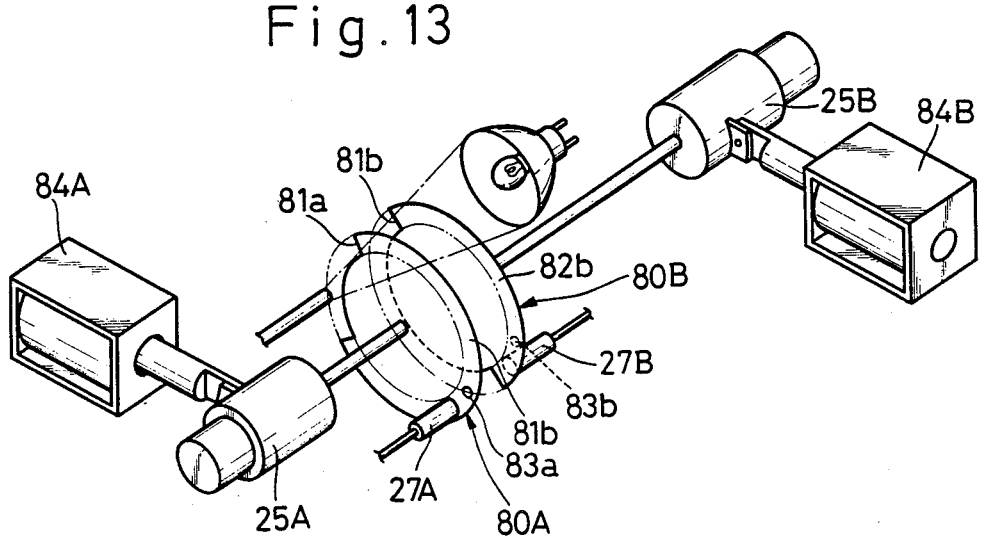
FIG. 13 is a perspective view showing a chopper control mechanism incorporated into a sixth embodiment of the invention
Figure 14:
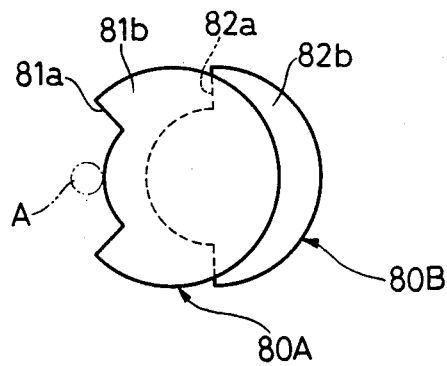
FIGS. 14 and 15 are front elevational views respectively showing different positional relationships between the chopper and luminous flux shown in FIG. 13.
Figure 15:
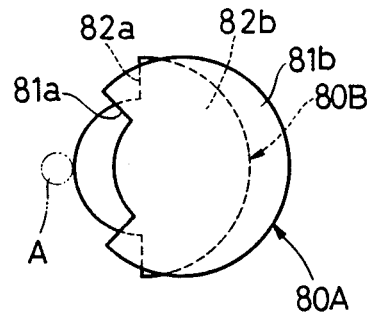
Figure 16:
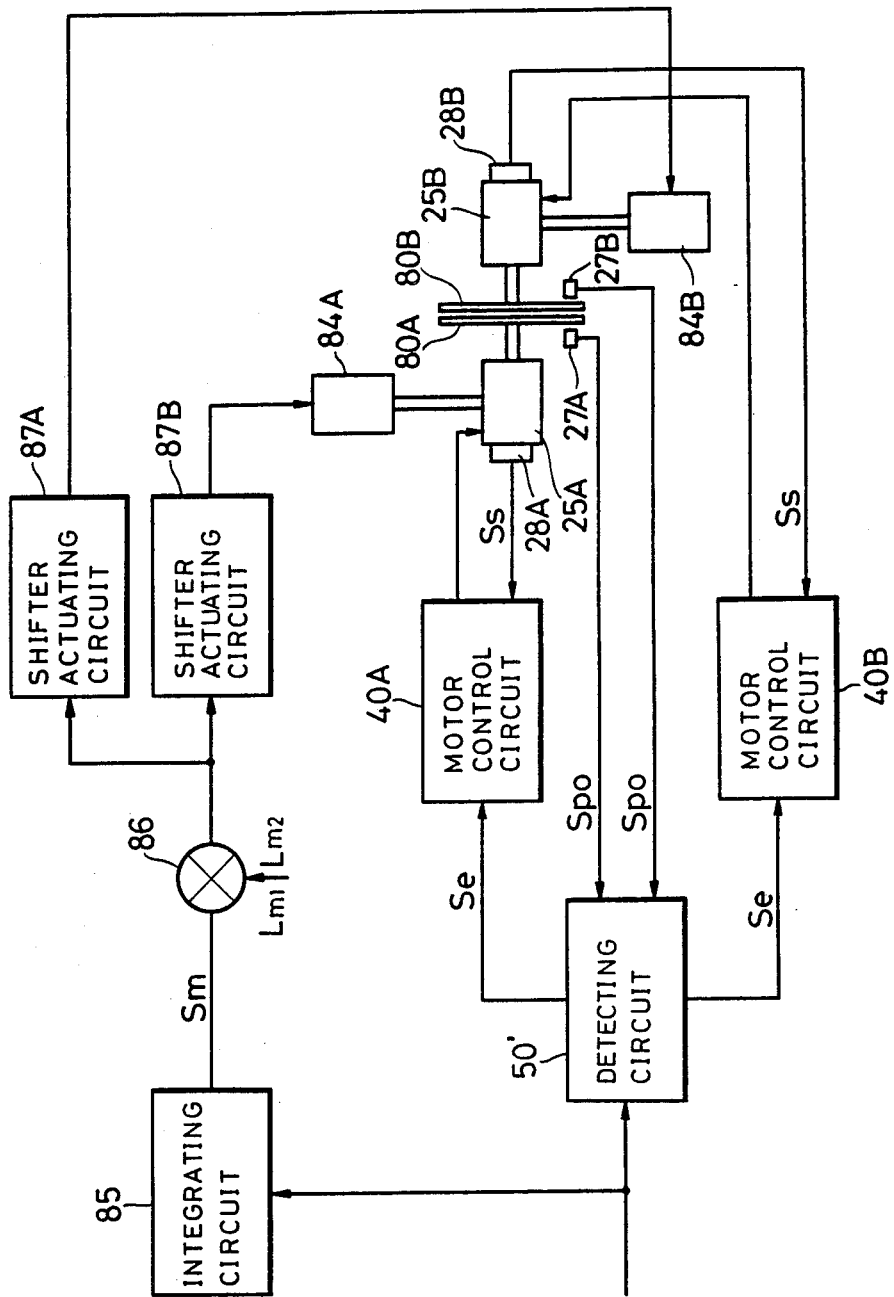
FIG. 16 is a block diagram showing an electric circuit for use in the chopper control mechanism shown in 13.

FIGS. 13 through 16 show a sixth embodiment of the invention, which is similar in basic technical idea to the fifth embodiment described with reference to FIGS. 9 through 12, but employs two choppers 80A and 80B having their respective rotational axes extending in coaxial or parallel relation to each other. The chopper 80A is formed at its peripheral portion with a first window 81a and a first shielding section 81b similar in angular in angular extent to those 81a and 81b of the chopper 80 of the fifth embodiment. The chopper 80B is formed at its peripheral portion with a second window 82a and a second shielding section 82b similar in angular extent to those 82a and 82b of the chopper 80 of the fifth embodiment. In the sixth embodiment shown in FIGS. 13 through 16, the choppers 80A and 80B are rotated by their respective electric motors 25A and 25B independent of each other. As shown in FIG. 13, a position sensor 27A is adapted to detect a reflective spot 83a provided at a specific position on the shielding section 81b of the chopper 80A and, similarly, a position sensor 27B is adapted to detect a reflective spot 83b provided at a specific position on the shielding section 82b of the chopper 80B. As shown in FIG. 16, similarly to the fifth embodiment, the detecting circuit 50' is operative in response to detected position signals Spo from the respective position sensors 27A and 27B and the frame synchronizing signal, to respectively supply the deviation signals Se, corresponding respectively to the choppers 80A and 80B, to motor control circuit 40A and 40B. The circuits 40A and 40B are operative in response to the respective deviation signals Se and respective speed signals Ss from speed sensors 28A and 28B respectively provided at the motors 25A and 25B, to respectively control the motors 25A and 25B.

Each of the choppers 80A and 80B is adjusted in its position in two steps by a corresponding one of shifters 84A and 84B. The shifters 84A and 84B are connected to their respective motors 25A and 25B from respective directions opposite to each other, and are actuated by respective shifter actuating circuits 87A and 87B.

When a level of a brightness signal from the integrating circuit 85 exceeds $Lm_1$, the comparator 86 outputs actuating signals respectively to the shifter actuating circuits 87A and 87B, to energize solenoids of the respective shifter 84A and 84B, so that, as shown in FIG. 14, the liminous flux A is located on the rotational locus of the first window 81a and the first shielding section 81b of the chopper 80A. Thus, the supply time duration of the illuminating light is shortened. When the brightness signal is lowered to a level lower than $Lm_2$, the comparator 86 outputs the relurn signal to deenergize the solenoids of the respective shifters 84A and 84B, so that, as shown in FIG. 15, the luminous flux A is located on the rotational locus of the second window 82a and the second shielding section 82b of the chopper 80B. Thus, the supply time duration of the illuminating light is lengthened.

Figure 17:
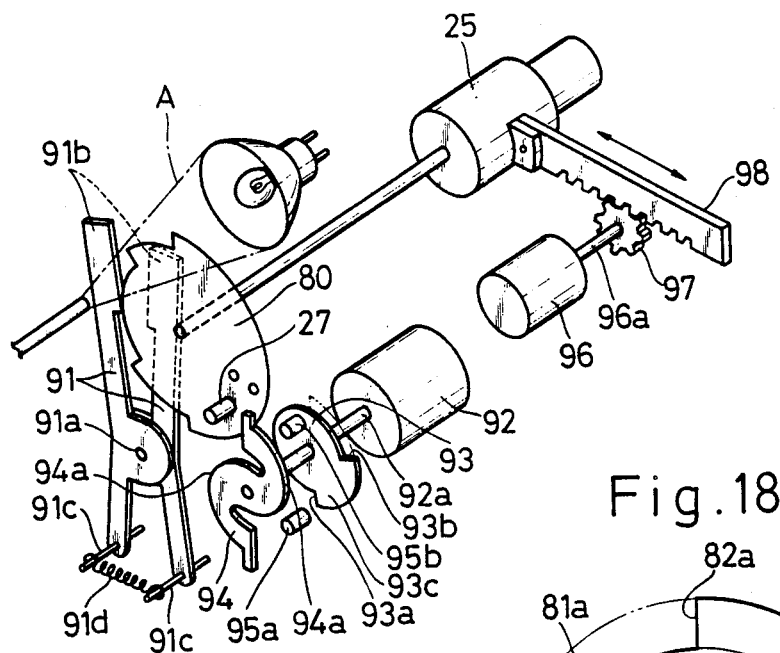
FIG. 17 is a perspective view showing a shield control mechanism and a chopper control mechanism incorporated into an seventh embodiment of the invention.
Figure 18:
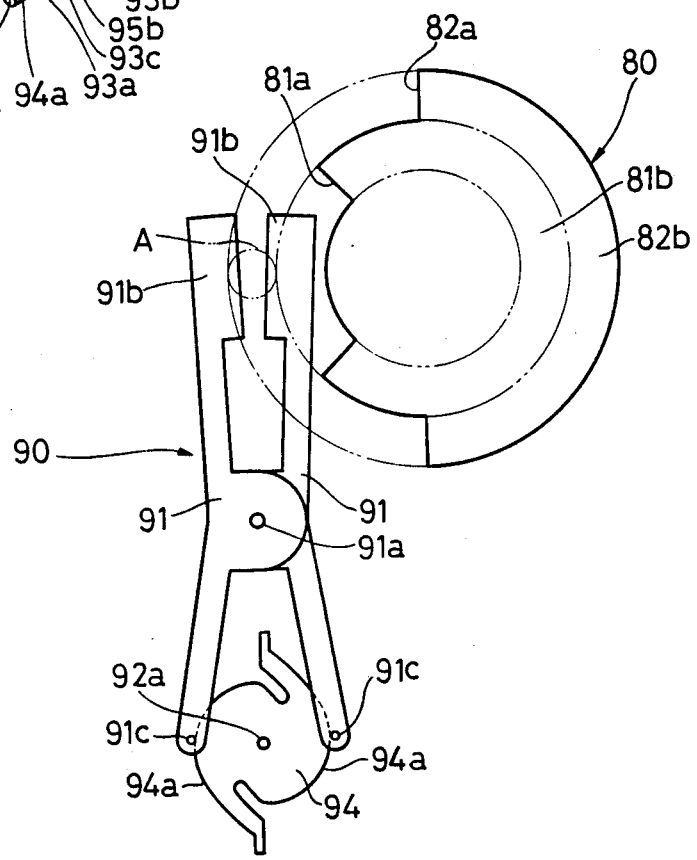
FIG. 18 is a front elevational view showing a positional relationship between the chopper, shielding members and luminous flux shown in FIG. 17.

FIGS. 17 through 19 show a seventh embodiment of the invention, which comprises restricting means 90 in addition to a chopper similar to that utilized in the fifth embodiment shown in FIGS. 9 through 12. Basic construction of the restricting means 90 is known per se. The restricting means 90 comprises a pair of restricting members 91 and 91 which are supported at their respective intermediate portions by a common shaft 91a for angular movement therearound. Each of the restricting members 91 is formed at its one end with a relatively wide shielding section 91b, and a corresponding one of pins 91c is attached to the other end of each of the restricting members 91. A spring 91b is connected between the pins 91c on the respective restricting members 91 to pull the pins 91c toward each other. The shielding sections 91b of the respective restricting members 91 are movable toward and away from each other to vary the cross-sectional area of the luminous flux A, to thereby adjust the passing amount of the illuminating light per unit time.

The restricting means 90 is adapted to be driven by an electric motor 92 having an output shaft 92a. A detecting plate 93 is fixedly mounted on an intermediate portion of the output shaft 92a, and a cam 94 is fixedly mounted on a free end of the output shaft 92a. The cam 94 has a pair of cam surfaces 94a which are adapted to abut respectively against the pins 91c provided on the respective restricting members 91.

The detecting plate 93 is generally in the form of a disc and is formed at its peripheral portion with a shielding section 93c extending through a predetermined angular extent and having a radius of curvature greater than that of the remaining section. Restriction sensors 95a and 95b such as a photosensor of a reflective type are arranged in the vicinity of the detecting plate 93, to respectively detect positions of different end edges 93a and 93b of the shielding sections 93c.

The locations, where the restriction sensors 95a and 95b are respectively set, determine an angular movement extent of the cam 94, i.e., an extent of the passing amount of the illuminating light adjusted by the pair of restricting members 91.

The chopper 80 and the motor 25 for rotating the same are constructed similarly to those of the fifth embodiment shown in FIGS. 9 through 12, but are adapted to be shifted by a stepping motor 96 in the direction perpendicular to the optical axis of the luminous flux A of the illuminating light. The stepping motor 96 has an output shaft 96a on which a pinion 97 is fixedly mounted, and a rack 98 is in mesh with the pinion 97. The rack 98 is guided by a guide mechanism (not shown) so as to be movable only in the longitudinal direction, and one end of the rack 98 is connected to the motor 25 for rotating the chopper 80.

The seventh embodiment includes an electric circuit shown in FIG. 19, which is similar to that of the fifth embodiment shown in FIG. 10, but a motor control cirbuit 100 for controlling the motor 92 is connected to the integrating circuit 85. Moreover, the restriction sensors 95a and 95b are connected to a motor control circuit 101 for controlling the stepping motor 96.

The seventh embodiment is devised, taking into consideration the following principle. That is, the brightness of the picture is in proportional relation to the amount of electric charges stored by the light receiving portion of the solid state image pickup element for each time duration of one field scanning, and the amount of electric charges stored is obtained by integrating, with the supply time duration of the illuminating light, the values obtained by multiplying the illuminated amount of light per unit time by the reflective efficiency (i.e., reflected amount of light per unit time received by the solid state image pickup element). Accordingly, if the reflective efficiency is high, the supply time duration of the illuminating light or the illuminated amount of light per unit time is reduced, and if the reflective efficiency is low, the supply time duration of the illuminating light or the illuminated amount of light per unit time is increased, so that it is possible to maintain the brightness of the picture to an appropriate level.

In the seventh embodiment shown in FIGS. 17 through 19, the passing amount of the illuminating light per unit time is regulated in a stepless manner over a predetermined range by the restricting means 90, and the supply time duration of the illuminating light is regulated in a stepped manner by the lateral movement or shift of the chopper 80. The restricting members 91 are angularly moved depending upon the brightness of the picture, and the chopper 80 is shifted depending upon the restricting degree of the restricting members 91, so that the restricting members 91 and the chopper 80 cooperate with each other to perform the adjustment.

Firstly, the fine adjustment due to the restricting members 91 on the basis of the brightness of the picture will be described. The picture signals from the picture circuit 30 (FIG. 1) are integrated by the integrating circuit 85, to detect the brightness of the picture. The detected brightness signal from the integrating circuit 85 is sent to the motor control circuit 100, which drivingly controls the restricting motor 92 such that the brightness signal is brought to a set level. As the cam 94 is rotated by the driving of the restricting motor 92, the opening degree between the shielding sections 91b of the respective restricting members 91 varies to vary the cross-sectional area of the luminous flux A, so that the passing amount of the illuminating light per unit time is regulated in a stepless manner. As the reflective efficiency is increased, the cam 94 is rotated in the clockwise direction as viewed in FIG. 18, and the pins 91c are moved away from each other to move the shielding sections 91b toward each other, so that the passing amount of the illuminating light is reduced. As the reflective efficiency is reduced, the cam 94 is rotated in the counterclockwise direction, to move the shielding sections 91b away from each other, so that the passing amount of light is increased. Thus, it is made possible to bring the brightness of the picture to a constant level.

The regulation due to the chopper 80 will next be described. The normal and reverse rotation of the stepping motor 96 is transmitted, through the pinion 97 and the rack 98, to the motor 25 and the chopper 80 to shift the same in a stepped manner by a constant amount in the direction perpendicular to the optical axis of the luminous flux A. The shift enables the supply time duration of the illuminating light to be controlled in two steps, similarly to the fifth embodiment shown in FIGS. 9 through 12.

The relationship between the regulation due to the restriction of the restricting members 91 and the regulation due to the shift of the chopper 80 will next be described. As discussed previously, when the cam 94 is rotated in the clockwise direction so as to reduce the amount of light passing between the restricting members 91, and the passing amount of light reaches the lower limit value of the adjusting range, one end edge 93a of the shielding section 93c of the detecting plate 93 interlocked with the cam 94 is detected by the restriction sensor 95a. The lower limit value detected signal is sent to the motor contorl circuit 101, whereby the stepping motor 96 is rotated in the normal direction by a constant amount to shift the rotating motor 25 and the chopper 80 toward the limunous flux A, to thereby regulate the supply time duration of the illuminating light so as to be reduced in half. This results in the reduction in half of the electric charges stored at the solid state image pickup element 16, and also in the reduction in half of the brightness level of the brightness signal. At this time, the motor control circuit 100 is operative in response to this brightness signal to control the restricting motor 92, to open the restricting members 91, to thereby double the passing amount of light as compared with that immediately before the lateral shift of the chopper 80. Thus, it is possible to eliminate the confusion due to the adjustment by the lateral shift of the chopper 80 for a short period of time. When the restricting members 96 are again closed, the amount of light can be reduced.

Moreover, when the cam 94 is rotated in the counterclockwise direction so as to increase the passing amount of light, and the upper limit value of the passing amount of light is reached, the other end edge 93b of the shielding section 93c of the detecting plate 93 is detected by the restriction sensor 95b. The upper limit value detected signal is sent to the motor control circuit 101, whereby the stepping motor 96 is rotated in the reverse direction by a constant amount to move the motor 25 and the chopper 80 away from the luminous flux A, so that the supply time duration of the illuminating light is doubled, and the brightness level of the brightness signal is temporarily doubled. At this time, the restricting members 91 are moved in the closing direction such that the amount of light is reduced in half as compared with that immediately before the lateral movement of the chopper 80. Accordingly, it is made possible to eliminate the confusion due to the adjustment by the lateral shift of the chopper 80 for a short period of time. When the restricting members 96 are again opened, the amount of light can be increased.

The ratio between the maximum value and the minimum value of the passing light amount adjusting range by the restricting members is made greater than the ratio between the first and second steps of the supply time durations of the illuminating light, to thereby prevent the hunting upon the lateral shift of the chopper 80.

Since the restricting means 90 is adjusted in a stepless manner, it is possible to cope with the fine fluctuation in the reflective efficiency, and it is made possible by the chopper 80 to substantially widen the stepless adjusting range of the picture brightness, so that it is possible to cope with great fluctuation in the reflective efficiency.

The present invention should not be limited to the specific embodiments described above, but various modifications and changes may be made to the invention. For example, such an endoscope may be utilized that an ocular portion is provided at the operating body; the light entering through the viewing window is transmitted to the ocular portion through a lens system and an optical fiber bundle; a television camera for the monitor television is connected to the ocular portion; an image from the endoscope is received by a solid state image pickup element of the television camera.

The position sensor should not be limited to the photosensor, but may be a proximity switch, for example. In this case, the chopper is formed of a non-magnetic material, and a magnet is attached to a specific position on a surface of the chopper.

The rotational speed of the motor may be detected by processing the detected position signals from the position sensor. In this case, the speed sensor is dispensed with, but in substitution therefor, a processing circuit for the detected position signals is required.

The chopper may be formed with a plurality of windows circumferentially equidistantly spaced from each other on the same rotational locus. In this case, at each time the chopper is rotated by one revolution, the frame scannings corresponding to the number of the windows are performed.

Not only the stationary picture on the monitor television is merely observed, but also may be recorded on an optical disc, or may be photographed by a camera with hood. In addition, without the use of the frame memory, one of the moving pictures projected on the monitor television, corresponding to one frame scanning, may be photographed by the camera with hood.

The frame synchronizing signals may be obtained by various means. For example, the vertical synchronizing signals may alternately be detected by a flip-flop, to obtain the frame synchronizing signals.

In the fifth to seventh embodiments shown in FIGS. 9 through 19, the rotational locus of each or the chopper may be moved out of the luminous flux of the illuminating light, to enable the illuminating light to be supplied continuously. In this case, it is possible for the illustrated embodiments to carry out the adjustment of the illuminating light supply time duration in three steps, and even if each or the chopper is provided with only one window in the radial direction, it is possible to carry out the adjustment in two steps.

In case where each or the chopper is formed with a plurality of windows along the radial direction, as is in the fifth to seventh embodiments shown in FIGS. 9 through 19, the reflective spot or magnet may be provided on a specific single position on each or the chopper. In this case, the position sensor is so arranged as to follow the lateral shift of each or the chopper such that the position sensor is always aligned with the rotational locus of the specific position.

In the seventh embodiment shown in FIGS. 17 through 19, the restriction sensor for detecting the boundary values of the light amount restricting range may be adapted to detect a specific position on another moving component of the restriction driving mechanism, for example, on the cam, or to detect a specific position on the restricting members. Moreover, a potentiometer may be mounted, as a restriction sensor, on the output shaft of the restricting motor or the cam shaft, to obtain the boundary value signals.

Furthermore, the restricting members may take any forms. For example, an arrangement may be such that a rotary plate in the form of a disc is rotated directly by a motor; a restricting elongated slot is formed in the rotary plate; and the radial width of the elongated slot is gradually increased or decreased correspondingly to the rotational angle of the rotary plate.

Brightness detecting means may be utilized, in which the detection of the brightness is performed by sampling the picture signals.

The present invention is applicable to either of medical and industrial endoscope apparatuses.

What is claimed is:

1. An electronic endoscope apparatus comprising:
   (a) an endoscope including an operating body, an inserting body extending from said operating body, and a viewing window and an illuminating window provided at respective appropriate locations of said inserting portion;
   (b) a solid state image pickup device including a light receiving portion for receiving images entering through said viewing window of said endoscope, and a memory portion for storing image signals from said light receiving portion;
   (c) circuit means for converting the image signals from said image pickup device into television picture signals of an interlaced scanning system;
   (d) a monitor television for displaying pictures on the basis of said television picture signals;
   (e) light source means:
   (f) an illuminating light transmitting optical system arranged within said endoscope, for transmitting an illuminating light from said light source means to said illuminating window;
   (g) chopper means disposed between an end of said illuminating light transmitting optical system and said light source means and including at least one light shielding section and at least one light transmitting section;
   (h) motor means for rotating said chopper means to cause said light shielding section and said light transmitting section of said chopper means to successively cross a luminous flux of the illuminating light, to thereby bring the illuminating light into the form of pulses; and
   (i) synchronizing circuit means for controlling the rotation of said motor means in such a manner that a center of supply time duration of each of the illuminating light pulses is brought into coincidence with a point of time at which the image signals to be offered to either one of odd and even field scannings are transferred from said light receiving portion to said memory portion of said image pickup device.

2. An electronic endoscope apparatus as defined in claim 1, wherein said image pickup device is arranged within said inserting portion of said endoscope and adjacent said viewing window.

3. An electronic endoscope apparatus as defined in claim 1, wherein said motor means has an output shaft, and said chopper means has a rotary axis extending in coaxial relation to said output shaft.

4. An electronic endoscope apparatus as defined in claim 3, wherein said chopper means is in the form of a disc formed at its peripheral portion with at least one window to define said light transmitting section.

5. An electronic endoscope apparatus as defined in claim 1, wherein said synchronizing circuit means includes:
   (a) detecting circuit means for detecting a rotational condition of said motor means; and
   (b) motor control circuit means operative in response to a detecting signal from said detecting circuit means for controlling said motor means.

6. An electronic endoscope apparatus as defined in claim 5, wherein said detecting circuit means includes a phase difference detecting circuit for detecting a phase difference between the image signal transferred point of time and a point of time at which a longitudinal center of said light transmitting section on a rotational locus thereof reaches a center of the luminous flux of the illuminating light.

7. An electronic endoscope apparatus as defined in claim 6, further comprising position sensor means for detecting a passage of a specific point on said chopper means,
said phase difference detecting circuit including:
   (a) a synchronizing signal generating circuit for generating a synchronizing signal every frame scanning;
   (b) a first comparing circuit for comparing a detected position signal from said position sensor, representative of the detection of the specific point on said chopper means, with the synchronizing signal from said synchronizing signal generating circuit;
   (c) a phase difference setting circuit for setting a phase difference; and
   (d) a second comparing circuit for comparing a phase difference signal from said first comparing circuit with a set phase difference signal from said phase difference setting circuit, to output a deviation signal therebetween to said motor control circuit means, said deviation signal being representative of a signal of the phase difference between the image signal transferred point of time and the point of time at which the longitudinal center of said light transmitting section on the rotational locus thereof reaches the center of the luminous flux of the illuminating light.

8. An electronic endoscope apparatus as defined in claim 5, wherein said detecting circuit means includes a brightness difference detecting circuit for detecting a difference between a brightness of the odd field and a brightness of the even field, to output a signal representative of the brightness difference to said motor control circuit means, to thereby control said motor means.

9. An electronic endoscope apparatus as defined in claim 8, wherein said brightness difference detecting circuit includes a first integrating circuit for integrating the television picture signals of the odd field, a second integrating circuit for integrating the television picture signals of the even field, and a comparing circuit for comparing respective integrated value signals from said first and second integrating circuits with each other to detect the brightness difference.

10. An electronic endoscope apparatus as defined in claim 9, wherein said brightness difference detecting circuit further includes;
 (a) a differentiating circuit for differentiating a brightness difference signal from said comparing circuit;
 (b) a mixing circuit for adding a differentiating signal from said differentiating circuit to the brightness difference signal to obtain a modified brighness difference signal.

11. An electronic endoscope apparatus as defined in claim 5, wherein said detecting circuit means includes:
 (a) a phase difference detecting circuit for detecting a phase difference between said image signal transferred point of time and a point of time at which a longitudinal center of said light transmitting section on the rotational locus thereof reaches a center of the luminous flux of the illuminating light;
 (b) a brightness difference detecting circuit for detecting a difference between a brightness of the odd field and a brightness of the even field; and
 (c) switching-over means for selectively connecting said phase difference detecting circuit and said brightness difference detecting circuit to said motor control circuit means,
wherein said switching-over means is arranged such that said motor means is controlled in response to a phase difference signal from said phase difference detecting circuit, within an initial unstable region of the driving of said motor means, and said motor means is controlled in response to a brightness difference signal from said brightness difference detecting circuit, during a stable region of the driving of said motor means.

12. An electronic endoscope apparatus as defined in claim 5, including:
 position sensor means for detecting a passage of the specific point on said chopper means;
 said detecting circuit means including a phase difference detecting circuit and a brightness difference detecting circuit for detecting a difference between a brightness of the odd field and a brightness of the even field; and
 said phase difference detecting circuit including:

(a) a synchronizing signal generating circuit for generating a synchronizing signal every frame scanning;
 (b) a first comparing circuit for comparing a detected position signal from said position sensor, representative of the detection of the specific point on said chopper means, with the synchronizing signal from said synchronizing signal generating circuit;
 (c) a phase difference setting circuit for setting a phase difference; and
 (d) a second comparing circuit for comparing a phase difference signal from said first comparing circuit with a set phase difference signal from said phase difference setting circuit, to output a deviation signal therebetween to said motor control circuit means, said deviation signal being representative of a signal of the phase difference between the image signal transferred point of time and the point of time at which the longitudinal center of said light transmitting section on the rotational locus thereof reaches the center of the luminous flux of the illuminating light,
 wherein the set phase difference in said phase difference setting circuit is regulated on the basis of a brightness difference signal from said brightness difference detecting circuit.

13. An electronic endoscope apparatus as defined in claim 1, including:
 shifting means for shifting said chopper means in a direction perpendicular to the luminous flux of the illuminating light, to adjust the supply time duration of each of said illuminating light pulses.

14. An electronic endoscope apparatus as defined in claim 13, wherein said chopper means is formed with a plurality of light transmitting sections continuous to each other in a radial direction, said light transmitting sections having their respective lengths on their respective rotational loci, which are different from each other.

15. An electronic endoscope apparatus as defined in claim 13, wherein said shifting means comprises a solenoid-actuated shifter having a rod connected to said motor means.

16. An electronic endoscope apparatus as defined in claim 13, wherein said shifting means comprises a motor, a pinion rotatively driven by said motor, and a rack in mesh with said pinion, said rack having one end thereof connected to said motor means.

17. An electronic endoscope apparatus as defined in claim 13, including a brightness detecting circuit for detecting a brightness of the picutre, said shifting means being controlled in response to a brightness signal from said brightness detecting circuit.

18. An electronic endoscope apparatus as defined in claim 13, wherein said chopper means includes a pair of choppers disposed between said light source means and the end of said illuminating light transmitting optical system, one of said pair of choppers being formed with said light transmitting section which is different in length on the rotational locus from that formed in the other of said pair of choppers, wherein said motor means includes a pair of motors drivingly connected respectively to said pair of choppers for rotating the same, and wherein said shifting means includes a pair of shifter mechanisms, one of said pair of shifter mechanisms being connected to one of said pair of choppers and one of said pair of motors for shifting the same, and the other of said pair of shifter mechanisms being connected to the other of said pair of choppers and the other of said pair of motors for shifting the same.

19. An electronic endoscope apparatus as defined in claim 13, including:
 restricting means for restricting a cross-sectional area of the luminous flux of the illuminating light, said restricting means together with said chopper means being disposed between said light source means and the end of said illuminating light transmitting optical system.

20. An electronic endoscope apparatus as defined in claim 19, including:
 a brightness detecting circuit for detecting a brightness of the picture; and
 a control circuit operative in response to a signal from said brightness detecting means for controlling said restricting means.

21. An electronic endoscope apparatus as defined in claim 19, wherein said restricting means is driven by a motor.

22. An electronic endoscope apparatus as defined in claim 21, including:
 a pair of restriction sensors for respectively detecting specific positions on at least one movable component of a transmitting system between said motor and said restricting means, to determine whether the cross-sectional area of the luminous flux reaches upper and lower limit values of a region to be adjusted by said restricting means, said shifting means being operative in response to respective detecting signals from said restriction sensors.

23. An electronic endoscope apparatus as defined in claim 22, wherein said movable component is a detecting plate fixedly mounted on an output shaft of said motor.

* * * * *